United States Patent
Ruan et al.

(10) Patent No.: US 12,161,700 B2
(45) Date of Patent: Dec. 10, 2024

(54) DRUG CARRIER, BRAIN-TARGETING NANODRUG BASED ON CRISPR GENE EDITING TECHNOLOGY AND PREPARATION METHOD AND USE THEREOF

(71) Applicant: Henan University, Kaifeng (CN)

(72) Inventors: Weimin Ruan, Kaifeng (CN); Mingzhu Jiao, Kaifeng (CN); Bingyang Shi, Kaifeng (CN); Meng Zheng, Kaifeng (CN)

(73) Assignee: Henan University (CN)

( * ) Notice: Subject to any disclaimer, the term of this patent is extended or adjusted under 35 U.S.C. 154(b) by 840 days.

(21) Appl. No.: 17/112,020

(22) Filed: Dec. 4, 2020

(65) Prior Publication Data

US 2021/0299228 A1   Sep. 30, 2021

(30) Foreign Application Priority Data

Mar. 24, 2020   (CN) .......................... 202010214295.8

(51) Int. Cl.
| | |
|---|---|
| A61K 38/46 | (2006.01) |
| A61K 31/7105 | (2006.01) |
| A61K 47/54 | (2017.01) |
| A61K 47/58 | (2017.01) |
| A61K 47/60 | (2017.01) |
| A61K 47/64 | (2017.01) |
| A61K 47/69 | (2017.01) |
| C08F 293/00 | (2006.01) |

(52) U.S. Cl.
CPC ........ *A61K 38/465* (2013.01); *A61K 31/7105* (2013.01); *A61K 47/549* (2017.08); *A61K 47/58* (2017.08); *A61K 47/60* (2017.08); *A61K 47/64* (2017.08); *A61K 47/6933* (2017.08); *C08F 293/005* (2013.01); *C08F 2438/03* (2013.01)

(58) Field of Classification Search
None
See application file for complete search history.

(56) References Cited

U.S. PATENT DOCUMENTS

2019/0136231 A1   5/2019   Morrissey et al.

FOREIGN PATENT DOCUMENTS

| CA | 3009389 A1 | 12/2018 |
|---|---|---|
| CN | 104758952 A | 7/2015 |
| CN | 106890343 A | 6/2017 |
| CN | 107557393 A | 1/2018 |
| CN | 107998081 A | 5/2018 |
| CN | 108143718 A | 6/2018 |
| CN | 108339124 A | 7/2018 |
| CN | 109880021 A | 6/2019 |
| CN | 109893660 A | 6/2019 |
| CN | 110101685 A | 8/2019 |
| CN | 110215522 A | 9/2019 |

OTHER PUBLICATIONS

Wan et al., "Material solutions for delivery of CRISPR/Cas-based genome editing tools: current status and future outlooks", Materials Today vol. 26, pp. 40-66 Jun. 2019.*

(Continued)

*Primary Examiner* — Anand U Desai
(74) *Attorney, Agent, or Firm* — Billion & Armitage

(57) ABSTRACT

The present disclosure provides a drug carrier, a brain-targeting nanodrug based on CRISPR gene editing technology and a preparation method and use thereof. The nanodrug contains nanoparticles prepared by coupling Cas9/sgRNA and drug carriers. The drug carrier includes a polymer mPEG-P (GPMA, FPMA) and a polymer Ang-PEG-PGPMA, wherein a structural formula of the mPEG-P (GPMA, FPMA) is:

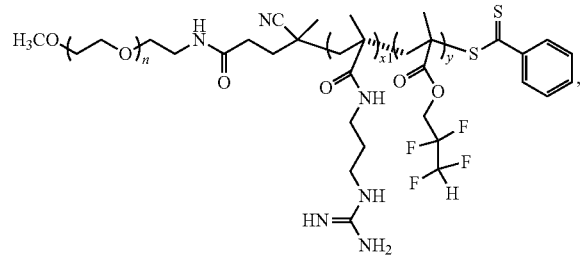

a structural formula of the polymer Ang-PEG-PGPMA is:

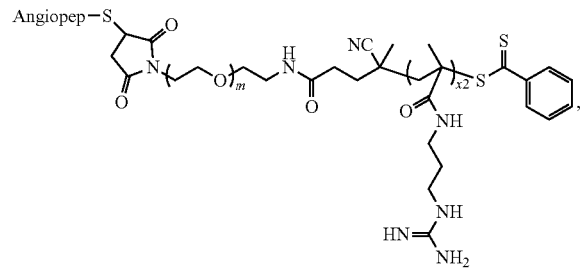

where n is 35-45, x1 is 15-20, y is 2-4, m is 75-85, and x2=x1. The guanidino group of the drug carrier can be combined with the ribonucleoprotein complex by electrostatic action, salt bridge formation, or hydrogen bonding action. Also provided are methods of suppressing and treating tumors at a gene level using the drug carrier to transport the therapeutic drug to the lesion site.

3 Claims, 4 Drawing Sheets

Specification includes a Sequence Listing.

(56) References Cited

OTHER PUBLICATIONS

Song et al., "Delivery of CRISPR/Cas systems for cancer gene therapy and immunotherapy", Advanced Drug Delivery Reviews 168 : 150-180 (Year: 2021).*
Doudna, "The promise and challenge of therapeutic genome editing", Nature vol. 578, pp. 229-236, Feb. 2020.*
First Office Action of Application No. CN202010214295.8.
First Search of priority application CN202010214295.8.
Notification to Grant Patent Right for Invention of priority application CN202010214295.8.
Supplementary search of priority application No. CN202010214295.8.

* cited by examiner

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
tacctacggc aaattgtgct                                              20

DRUG CARRIER, BRAIN-TARGETING NANODRUG BASED ON CRISPR GENE EDITING TECHNOLOGY AND PREPARATION METHOD AND USE THEREOF

CROSS-REFERENCE TO RELATED APPLICATION

The present disclosure claims priority of Chinese patent application with the filing number 2020102142958 filed on Mar. 24, 2020 with the Chinese Patent Office, and entitled "Drug Carrier, Brain-targeting Nanodrug Based on CRISPR Gene Editing Technology and Preparation Method and Use thereof", the contents of which are incorporated herein by reference in entirety.

SEQUENCE LISTING

The instant application contains a Sequence Listing which has been submitted electronically in ASCII format and is hereby incorporated by reference in its entirety. Said ASCII copy, created on Jan. 15, 2021, is named 920_027US1_SLSEQUENCE_LISTING.txt and is 595 bytes in size.

TECHNICAL FIELD

The present disclosure relates to the field of nanodrugs, in particular to a drug carrier, a brain-targeting nanodrug based on CRISPR gene editing technology and a preparation method and use thereof.

BACKGROUND ART

The cerebral glioma is a primary intracranial malignant tumor. Its incidence is 35.2-61.0% of that of intracranial tumors, and it has the characteristics such as high incidence, high relapse rate, high mortality, and low cure rate. Current clinical means for treating glioma mainly include surgery, radiotherapy, chemotherapy and other means.

The blood brain barrier (BBB) makes the human cerebral glioma become one of the most intractable tumors in cancer treatment. As a self-balancing defensive mechanism of brain, on one hand, BBB ensures the central nervous system to be protected from foreign substances, maintains a high-efficient steady state, and meanwhile inputs nutrients into the brain; on the other hand, the dense structure of BBB also hinders the therapeutic drug from entering the brain through non-invasive administration. Therefore, the top priority for treating brain diseases is to discover and research drugs or targeting molecules that can help nanodrug break through BBB.

SUMMARY

In a first aspect, the present disclosure provides a drug carrier, including a polymer mPEG-P (GPMA, FPMA) and a polymer Ang-PEG-PGPMA, wherein a structural formula of the mPEG-P (GPMA, FPMA) is:

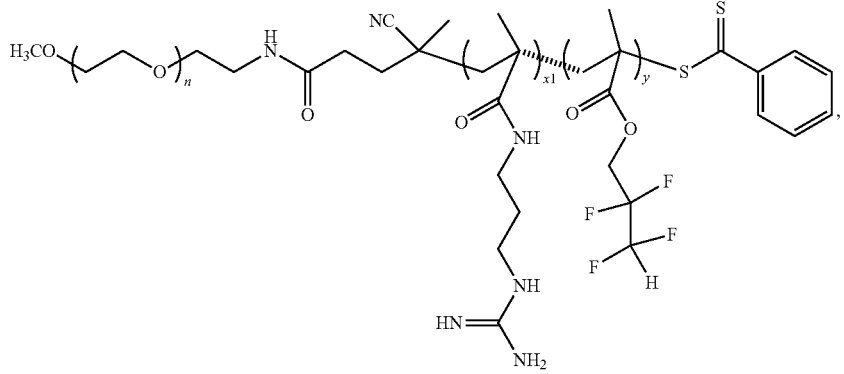

a structural formula of the polymer Ang-PEG-PGPMA is:

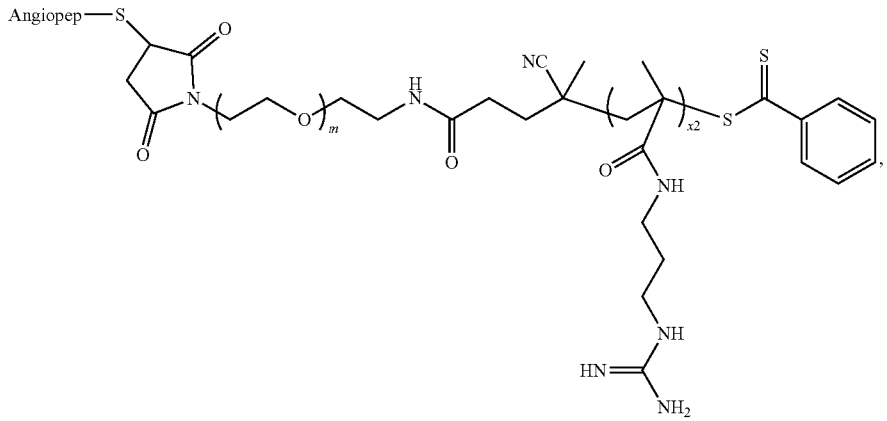

where n is 35-45, x1 is 15-20, y is 2-4, m is 75-85, and x2=x1.

In a second aspect, the present disclosure provides a brain-targeting nanodrug based on CRISPR gene editing technology, including nanoparticles obtained by coupling a therapeutic drug with the drug carrier according to the first aspect.

In a third aspect, the present disclosure provides a method for preparing the brain-targeting nanodrug based on CRISPR gene editing technology according to the second aspect, including:

Step a. dissolving the polymer mPEG-P (GPMA, FPMA) and the polymer Ang-PEG-PGPMA in a buffer solution to obtain a mixed solution A; and Step b. adding Cas9/sgRNA to the mixed solution A, so as to obtain by reaction nanoparticles Ang-NP@Cas9/sgRNA.

BRIEF DESCRIPTION OF DRAWINGS

In order to illustrate the technical solutions of the examples of the present disclosure more clearly, the accompanying drawings which need to be used in the examples will be briefly introduced below, and it should be understood that the following accompanying drawings merely show some examples of the present disclosure, thus they should not be considered as limitation to the scope of the present disclosure.

DETAILED DESCRIPTION OF EMBODIMENTS

Figure 1:
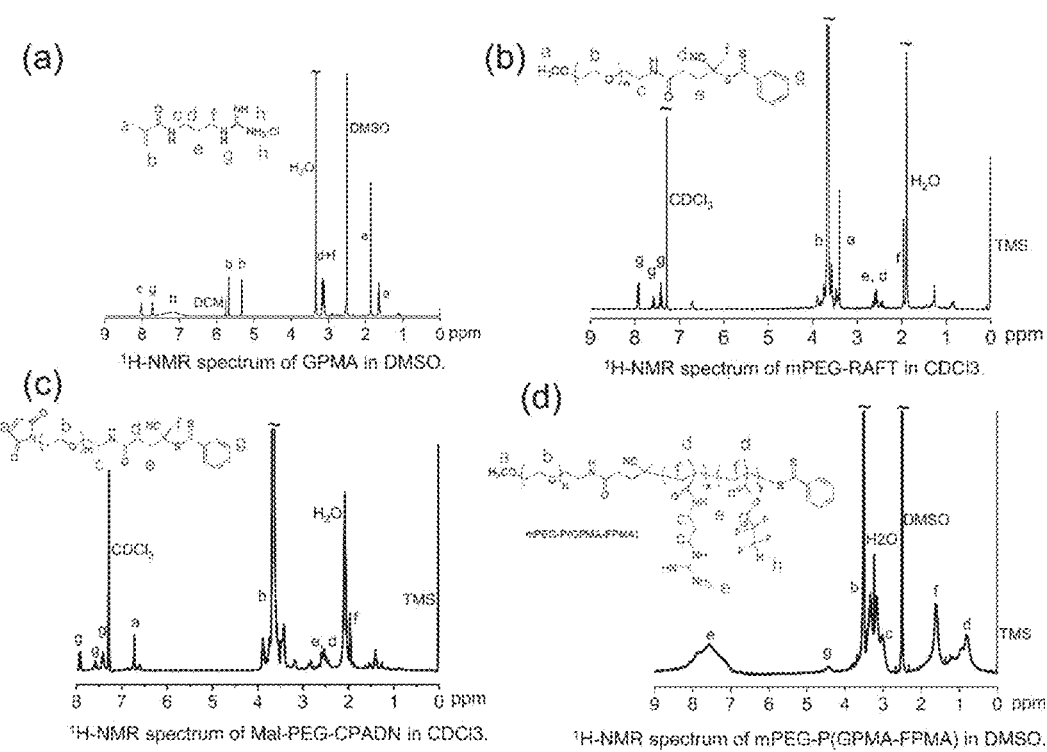
FIG. 1 is a 1H-NMR spectrum, wherein (a) in FIG. 1 is a 1H-NMR spectrum of a GPMA monomer, (b) in FIG. 1 is a 1H-NMR spectrum of an mPEG-CPADN, (c) in FIG. 1 is a 1H-NMR spectrum of an Mal-PEG-CPADN, and (d) in FIG. 1 is a 1H-NMR spectrum of an mPEG-P (GPMA-FPMA).

As used herein, the term "prepared from . . . " is synonymous with "comprising". The term "comprising", "including", "having", "containing" or any other derivatives thereof, as used herein, are intended to cover non-exclusive inclusion. For example, a composition, step, method, article or apparatus comprising the listed elements is not necessarily only limited to those elements, but may include other elements not explicitly listed or elements inherent to such composition, step, method, article or apparatuses.

The conjunction "consisting of . . . " excludes any unspecified element, step or component. If used in a claim, this phrase will make the claim be closed, so that the claim does not contain materials other than those described, but conventional impurities related thereto are excluded. When the phrase "consisting of . . . " appears in the clause of the claim rather than immediately after the subject matter, it only defines the elements described in the clause; and other elements are not excluded from said claim as a whole.

When the amount, concentration, or other values or parameters are expressed in a range, a preferred range, or a series of range defined by an upper preferred limit value and a lower preferred limit value, this should be understood as specifically disclosing all ranges formed by any pair of an upper value or a preferred value in any range and a lower value or a preferred value in any range, regardless of whether this range is separately disclosed. For example, when the range "1-5" is disclosed, the range described should be interpreted to include the ranges "1-4", "1-3", "1-2", "1-2 and 4-5", "1-3 and 5" etc. When a numerical range is described herein, unless otherwise specified, the range is intended to include its end values and all integers and fractions within this range.

In these examples, unless otherwise specified, all of the parts and percentages are counted by mass.

"Part by mass" denotes basic metering unit representing mass proportional relationships of a plurality of components, one part may denote any unit mass, for example, one part may represent 1 g, or may represent 2.689 g, etc. Assuming that the part by mass of a component A is a parts, and the part by mass of a component B is b parts, it means that the ratio of the mass of the component A to the mass of the component B is a:b. Alternatively, it means that the mass of the component A is ak, and the mass of the component B is bK (K is any number, and represents a multiplication factor). It should not be misunderstood that, unlike mass fraction, the sum of parts by mass of all components is not limited to 100 parts.

"And/or" is used to mean that one or both of the illustrated situations may occur, for example, A and/or B include (A and B) and (A or B).

"GPMA" refers to a guanidine monomer with a structural formula:

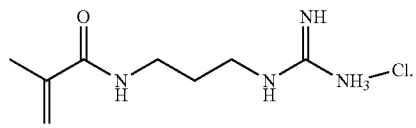

"FPMA" refers to 2,2,3,3-tetrafluoropropyl methacrylate with the structural formula

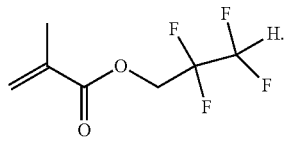

"CPADN" refers to 4-cyano-4-(phenylthioformylthio) pentanoic acid with the structural formula

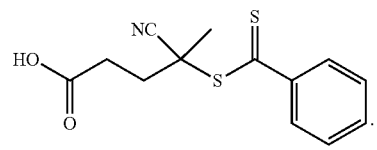 [SMILES: CC(C#N)(CCC(=O)O)SC(=S)c1ccccc1]

An object of the present disclosure is to provide a drug carrier, a brain-targeting nanodrug based on CRISPR gene editing technology and a preparation method and use thereof.

In order to achieve the above object, the present disclosure provides following technical solutions.

In a first aspect, the present disclosure provides a drug carrier, including a polymer mPEG-P (GPMA, FPMA) and a polymer Ang-PEG-PGPMA, wherein a structural formula of the mPEG-P (GPMA, FPMA) is:

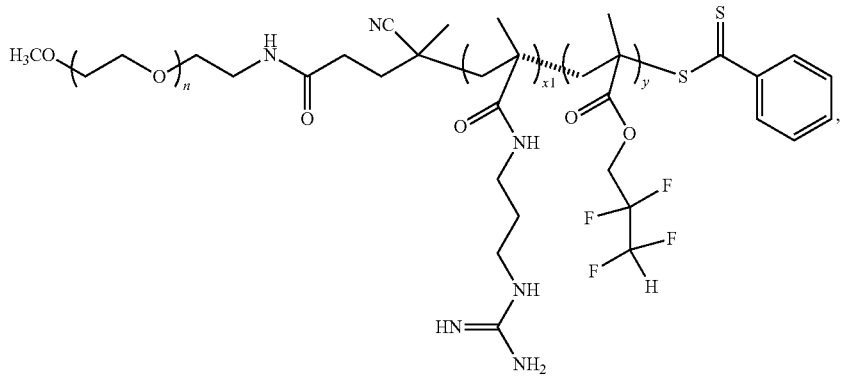

a structural formula of the polymer Ang-PEG-PGPMA is:

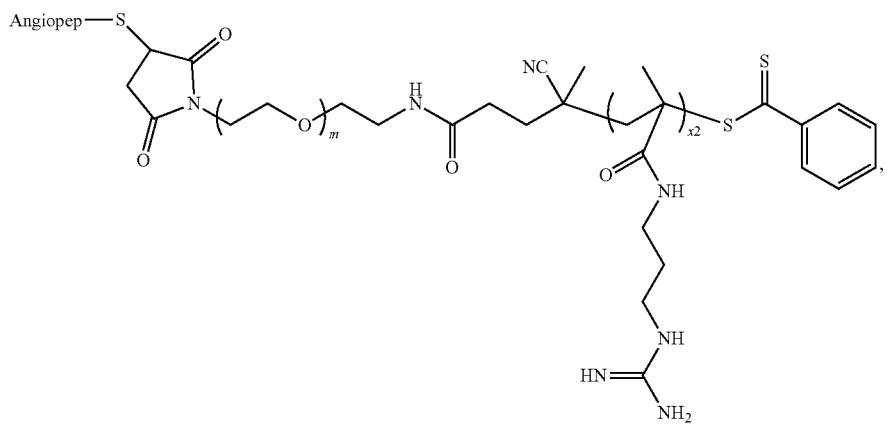

where n is 35-45, x1 is 15-20, y is 2-4, m is 75-85, and x2=x1.

As a further improvement of the above technical solution, the polymer mPEG-P (GPMA, FPMA) is mPEG$_{2K}$-P (GPMA$_{3K-4K}$, FPMA$_{0.5K-1K}$).

As a further improvement of the above technical solution, the polymer Ang-PEG-PGPMA is Ang-PEG$_{3.4K}$-PGPMA$_{4K}$.

In a second aspect, the present disclosure provides a brain-targeting nanodrug based on CRISPR gene editing technology, including nanoparticles obtained by coupling a therapeutic drug with the drug carrier according to the first aspect.

As a further improvement of the above technical solution, the therapeutic drug is Cas9/sgRNA, and the Cas9/sgRNA is obtained by complexing Cas9 protein and sgRNA.

As a further improvement of the above technical solution, the sgRNA is sgRNA targeting oncogene PLK1.

As a further improvement of the above technical solution, a sequence of the sgRNA targeting the oncogene PLK1 is as represented by SEQ ID NO. 1.

As a further improvement of the above technical solution, in mole part, in the Cas9/sgRNA, the ratio of the Cas9 protein to the sgRNA is 1:(1-1.5).

As a further improvement of the above technical solution, in mole part, the nanoparticles contain 1 part of Cas9/sgRNA, 1-3 parts of mPEG-P (GPMA, FPMA) and 4-12 parts of Ang-PEG-PGPMA.

In a third aspect, the present disclosure provides a method for preparing the brain-targeting nanodrug based on CRISPR gene editing technology according to the second aspect, including:

Step a. dissolving the polymer mPEG-P (GPMA, FPMA) and the polymer Ang-PEG-PGPMA in a buffer solution to obtain a mixed solution A; and Step b. adding Cas9/sgRNA to the mixed solution A, so as to obtain by reaction nanoparticles Ang-NP@Cas9/sgRNA.

As a further improvement of the above technical solution, the buffer solution is any one selected from a HEPES buffer solution and a PBS buffer solution.

As a further improvement of the above technical solution, the molar concentration of the buffer solution is 10-50 mM.

As a further improvement of the above technical solution, the pH of the buffer solution is 7.4-8.0.

As a further improvement of the above technical solution, a condition of the reaction in step b is well mixing and standing at room temperature.

As a further improvement of the above technical solution, the standing is carried out for 30-120 min.

In a fourth aspect, the present disclosure provides use of the brain-targeting nanodrug based on CRISPR gene editing technology according to the second aspect in preparation of a tumor treatment drug.

As a further improvement of the above technical solution, the tumor is cerebral glioma.

Beneficial effects of the present disclosure: the Angiopep polypeptide in the drug carrier provided by the present disclosure helps penetrate BBB and target tumor cells, PEG can effectively prolong the blood circulation period and have good biocompatibility, the guanidino Gut can be combined with the ribonucleoprotein complex not only by electrostatic action but also by forming salt bridge and hydrogen bonding action, a small amount of fluorine can enhance the stability of the nanodrug, and greatly prolong pharmacokinetic half-life of the nanodrug. Using this drug carrier can effectively transport the therapeutic drug to the lesion site.

The brain-targeting nanodrug based on CRISPR gene editing technology provided in the present disclosure contains the nanoparticles prepared by coupling Cas9/sgRNA and drug carriers. The Cas9/sgRNA has high cutting efficiency, Angiopep polypeptide in the drug carriers helps penetrate the blood brain barrier (BBB) and target the brain tumor cells. PEG can effectively prolong the blood circulation period and have good biocompatibility, the guanidino Gut can be combined with the ribonucleoprotein complex not only by electrostatic action but also by forming salt bridge and hydrogen bonding action, a small amount of fluorine can enhance the stability of the nanodrug, and greatly prolong pharmacokinetic half-life of the nanodrug. Using this drug carrier can effectively transport the therapeutic drug to the lesion site. The nanodrug may suppress and treat tumors at the gene level.

The present disclosure provides a drug carrier, a brain-targeting nanodrug based on CRISPR gene editing technology and a preparation method and use thereof. Specifically, the present disclosure provides the following technical solution.

In a first aspect, the present disclosure provides a drug carrier, including a polymer mPEG-P (GPMA, FPMA) and a polymer Ang-PEG-PGPMA;

a structural formula of the mPEG-P (GPMA, FPMA) is:

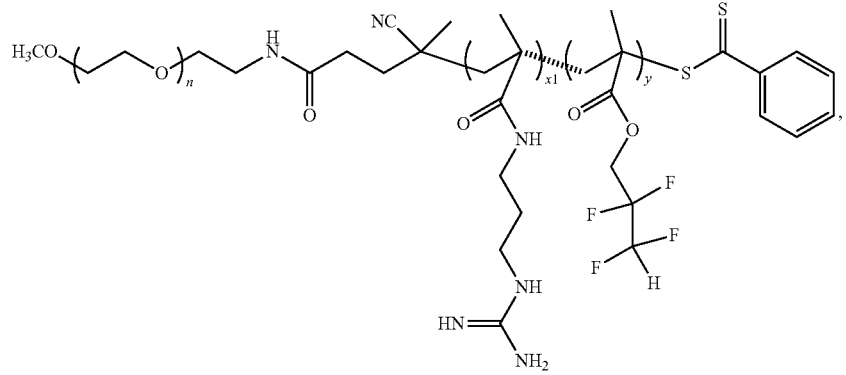

a structural formula of the polymer Ang-PEG-PGPMA is:

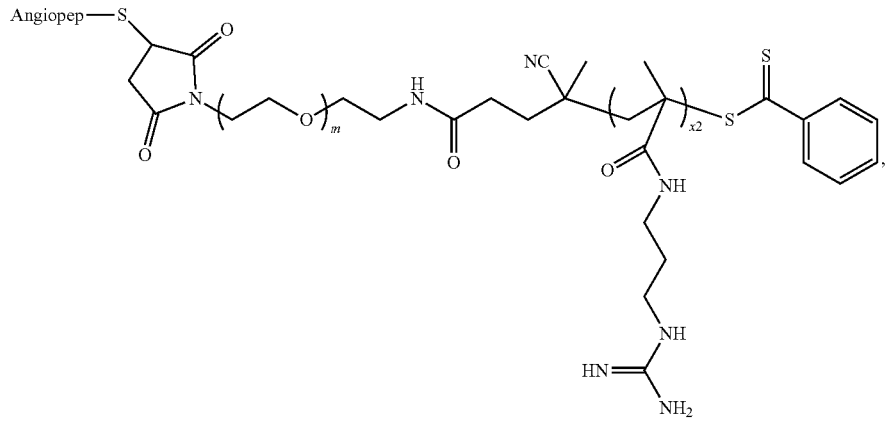

where n is 35-45, x1 is 15-20, y is 2-4, m is 75-85, and x2=x1.

The Angiopep polypeptide in the drug carrier of the present disclosure helps penetrate BBB and target tumor cells, PEG can effectively prolong the blood circulation period and have good biocompatibility, the guanidino Gut can be combined with the ribonucleoprotein complex not only by electrostatic action but also by forming salt bridge and hydrogen bonding action, a small amount of fluorine can enhance the stability of the nanodrug, and greatly prolong pharmacokinetic half-life of the nanodrug. Using this drug carrier can effectively transport the therapeutic drug to the lesion site.

Optionally, the polymer mPEG-P (GPMA, FPMA) is mPEG$_{2K}$-P (GPMA$_{3K-4K}$, FPMA$_{0.5K-1K}$).

Optionally, the polymer Ang-PEG-PGPMA is Ang-PEG$_{3.4K}$-PGPMA$_{4K}$.

In a second aspect, the present disclosure provides a brain-targeting nanodrug based on CRISPR gene editing technology, including nanoparticles obtained by coupling a therapeutic drug with the drug carrier according to the first aspect.

Optionally, the therapeutic drug is a complex Cas9/sgRNA, and the Cas9/sgRNA is obtained by complexing Cas9 protein and sgRNA.

Optionally, the sgRNA is sgRNA targeting oncogene PLK1.

Optionally, a sequence of the sgRNA targeting the oncogene PLK1 is as represented by SEQ ID NO. 1.

Polo-like kinase I (PLK1) is a serine-threonine protein kinase, and plays an important role in the cell cycle. Studies have found that the expression of PLK1 in cerebral glioma is significantly higher than that in normal cells, and inhibiting expression of PLK1 can significantly inhibit the growth of tumors, without significant inhibitory effect on normal cells. To this end, the gene PLK1 is chosen for gene editing, and tumor is suppressed and treated at the gene level. Cas9/sgRNA obtained by complexing sgRNA with the sequence as represented by SEQ ID NO. 1 and the Cas9 protein targets the oncogenic gene PLK1 gene, and has high-efficiency capacity of cutting PLK1 gene.

Optionally, in the Cas9/sgRNA, the ratio of Cas9 protein to sgRNA is 1:(1-1.5) in mole part.

Optionally, the nanoparticles contain 1 part of Cas9/sgRNA, 1-3 parts of mPEG-P (GPMA, FPMA) and 4-12 parts of Ang-PEG-PGPMA in mole part. Under this ratio, the nanoparticles prepared have a better particle size, and the drug is loaded by using fewer materials.

In a third aspect, the present disclosure provides a method for preparing the brain-targeting nanodrug based on CRISPR gene editing technology in the second aspect, including:

Step a. dissolving the polymer mPEG-P (GPMA, FPMA) and the polymer Ang-PEG-PGPMA in a buffer solution to obtain a mixed solution A; and Step b. adding Cas9/sgRNA to the mixed solution A, so as to obtain by reaction nanoparticles Ang-NP@Cas9/sgRNA.

The raw materials in the above preparation method can be synthesized by oneself or purchased directly. The reaction condition of the preparation method in the present disclosure is mild, and the operation is simple.

Optionally, the buffer solution is any one selected from a HEPES buffer solution and a PBS buffer solution.

Optionally, the molar concentration of the buffer solution is 10-50 mM.

Optionally, the pH of the buffer solution is 7.4-8.0.

Optionally, condition of the reaction in step b is well mixing and standing at room temperature; and preferably, the standing time is 30-120 min.

In a fourth aspect, the present disclosure provides use of the brain-targeting nanodrug based on CRISPR gene editing technology according to the second aspect in preparation of a tumor treatment drug; and preferably, the tumor is cerebral glioma.

Embodiments of the present disclosure will be described in detail below in combination with specific examples, while a person skilled in the art will understand that the following examples are merely for illustrating the present disclosure, but should not be considered as limitation on the scope of the present disclosure. If no specific conditions are specified in the examples, they are carried out under normal conditions or conditions recommended by manufacturers. If manufacturers of reagents or apparatuses used are not specified, they are conventional products commercially available.

Example 1

Preparation Method of Nanodrug

In the present example, the nanodrug is a nanoparticle Ang-NP@Cas9/sgRNA, the preparation method of the nanoparticle includes: in vitro transcription of sgRNA, synthesis of high molecular polymer and preparation of nanoparticles, and the target sequence of the sgRNA obtained from transcription is TACCTACGGCAAATTGTGCT (SEQ ID NO. 1). Specific steps are as follows:

1. In vitro transcription of sgRNA

The in vitro transcription simulated the environment of in vivo transcription, and there was no RNase during the whole operation, for the purpose of preventing the transcripted sgRNA from degradation, and the samples should be subpackaged and stored in a −80° C. refrigerator. Specific steps are as follows:

1.1 Annealing oligo (overall system 20 μL)

| 10 X Taq Buffer | 3 μL |
|---|---|
| Gene-specific oligo (100 μM)/Luc-F | 5 μL |
| Constant oligonucleotide (100 μM)/Luc-R | 5 μL |
| DEPC water | 14 μL |
| 2.5 mM dNTP | 3 μL |

After being at 95° C. for 5 min, the resultant was placed in room temperature overnight (or boiling water was naturally cooled to room temperature).

1.2 Adding 1 μL of Taq enzyme (10×PCR polymeranse) to react at 37° C. for 1 h.

1.3 Performing DNA purification (Cwbio Clean up kit), performing 4% agarose gel electrophoresis verification after purification, and storing the purified DNA in a −20° C. refrigerator.

1.4. In vitro transcription of sgRNA

The transcription system was as follows:

| DNA template (600-1000 ng) | |
|---|---|
| 10X Reaction Buffer | 1.5 μL |
| GTP | 1.5 μL |
| CTP | 1.5 μL |
| UTP | 1.5 μL |
| ATP | 1.5 μL |
| T7RNA polymerase mix | 1.5 μL |
| DEPC water | make up to 20 μL |

Mixing thoroughly at 37° C. overnight, then adding 10 μL of DNA Buffer and 70 μL of DEPC water, 1 μL of DNase, to react at 37° C. for 1 h.

1.5 Purifying RNA using a Beyotime Trizon kit, and storing the purified samples in a −80° C. refrigerator.

2. Synthesis of high-molecular polymer 2.1 Synthesis of polymer mPEG$_{2K}$-P (GPMA$_{4K}$, FPMA$_{0.6K}$)

The synthetic route was as follows:

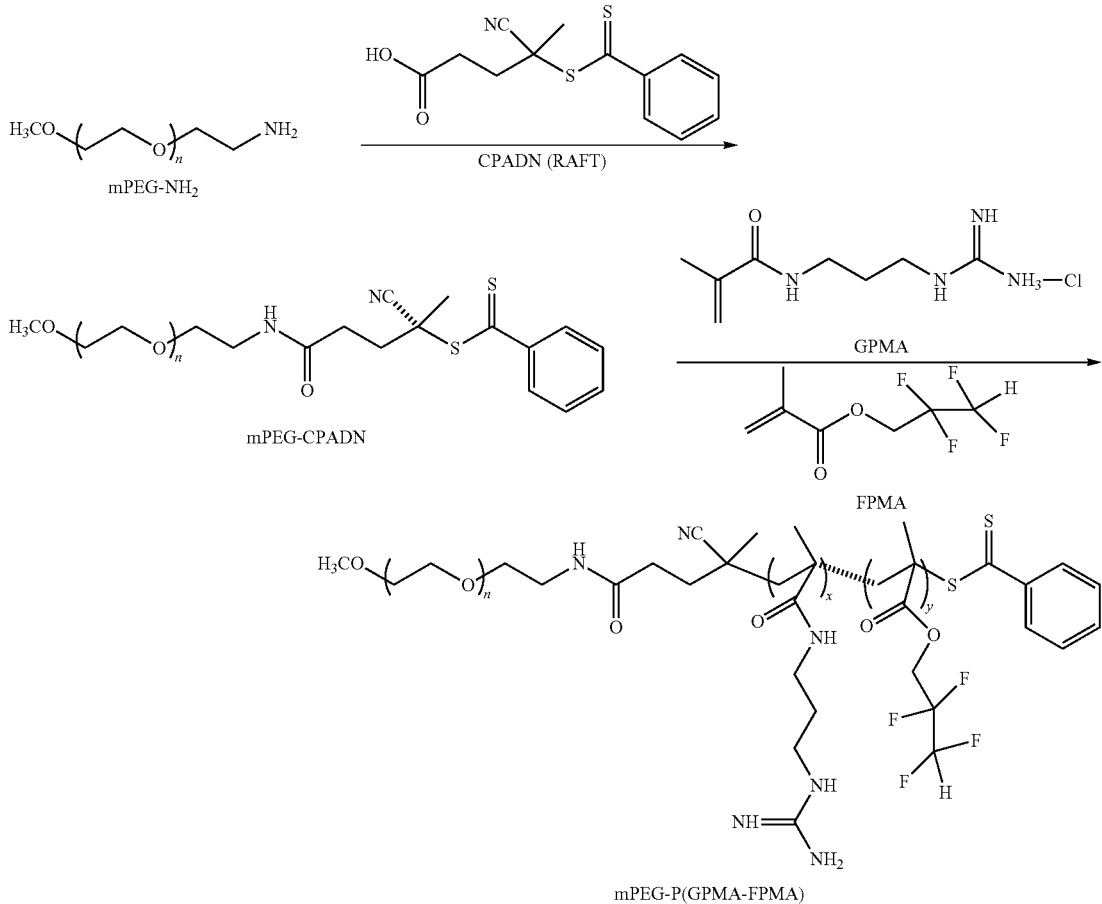

Specific steps were as follows:

2.1.1 Preparation of GPMA Monomer

1) To 16 mL of DMF adding APM (1.0 g, 5.6 mmol), H-pyrazde-carboxamidrine (0.82 g, 5.6 mmol), hydroquinone (10 mg), adding TEA (1230 mg, 12.3 mmol), and then stirring the resultant at room temperature for 24 h.

2) Stopping the reaction, centrifuging the reaction solution (8000 rpm, 5 min), collecting the supernatant, and filtering the supernatant using a 0.22 μm filter head to remove insoluble substances.

3) Then adding diethyl ether (100 mL) for washing, centrifuging (8000 rpm, 5 min), and collecting precipitate.

4) Washing the precipitate twice with 20 mL of acetonitrile, and 1 mL of TEA, and collecting the precipitate.

5) Washing the precipitate once with dichloromethane (30 mL), and finally washing once with diethyl ether, followed by vacuum-drying to obtain a light yellow transparent tacky product, and introducing nitrogen and storing the product at −20° C. in a light-tight condition.

2.1.2 Synthesis of mPEG$_{2K}$-CPADN

Reacting mPEG-NH$_2$ and CPADN in a molar ratio of 1:3, adding mPEG-NH$_2$ and CPADN-NHS in mixture into a single-neck flask, stirring the resultant at room temperature for 10 h, filtering the resultant with 0.22 μm filter head, and precipitating with ice diethyl ether (8000 rpm, 4° C., 5 min, washing until the supernatant was colorless), dissolving by 3 mL of dichloromethane each time, and adding the resultant dropwise to ice diethyl ether to precipitate, and washing.

2.1.3 Synthesis of polymer mPEG$_{2K}$-P (GPMA$_{4K}$, FPMA$_{0.6K}$)

A. The molar ratio of FPMA, GPMA, to CPADN was 8:30:1.

Dissolving GPMA (600 μmol), FPMA (140 μmol), PEG-CPADN (20 μmol), AIBN (3 μmol) in DMF, respectively, adding the mixture to a reaction kettle, wherein AIBN is added finally, and after adding AIBN, warming an oil bath pan slowly to 65° C. and stirring the resultant for 48 h.

B. Dialyzing with a dialysis bag of 3500 D using water, wherein water was changed for 48 h, every 2 h, removing excess unbound GPMA through dialysis, and finally drying through vacuum lyophilization, and storing the sample at −20° C. in a light-tight condition.

2.2 Synthesis of polymer Ang-PEG$_{3.4K}$-PGPMA$_{4K}$ (the method is the same as in 2.1).

The synthetic route was as follows:

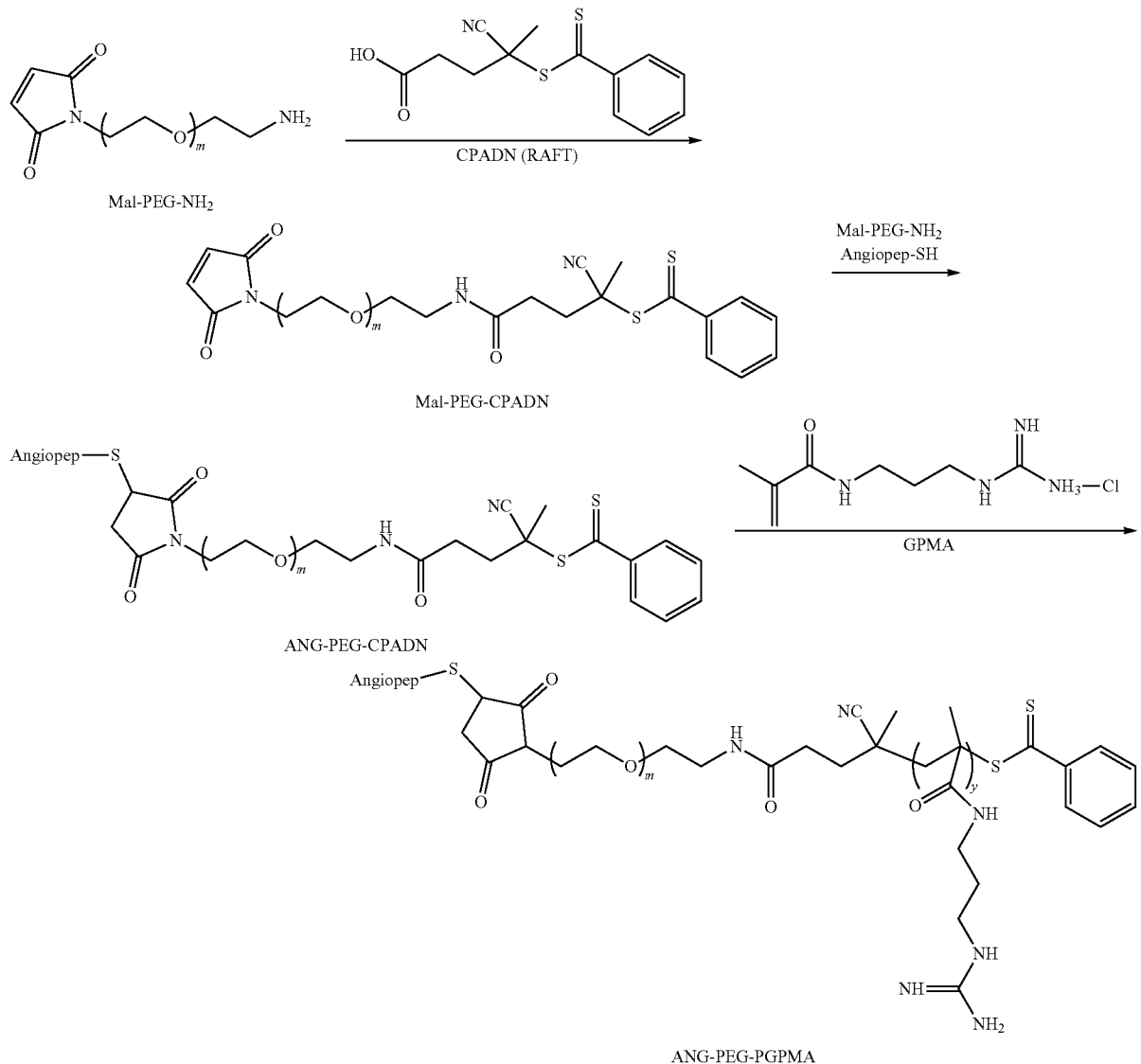

Specific steps were as follows:
1) Synthesis of Mal-PEG$_{3.4K}$-CPADN
A. Activation of CPADN
CPADN, NHS, DCC, and TEA were reacted in a ratio of 1:1:1.2:10 in molar ratio.

Dissolving CPADN (0.375 mmol, 37 mg), NHS (0.4125 mmol, 15.2 mg), DCC (0.4125 mmol, 32.6 mg), TEA (3.75 mmol, 150 μL), and NHS in 1 mL of DMF, dissolving CPADN in 10 mL of methylene dichloride, adding triethylamine, adding DCC slowly dropwise, wherein an ice bath was needed, when the ice slowly melted to room temperature, removing the ice bath, and stirring the resultant overnight.

B. Adding Mal-PEG-NH$_2$ (44 mmol, 150 mg), stirring the resultant at room temperature for 10 h, filtering the resultant with 0.22 μm filter head, and precipitating with ice diethyl ether (8000 rpm, 4° C., 5 min, washing until the supernatant was colorless), dissolving by 3 mL of dichloromethane each time, and adding the resultant dropwise to ice diethyl ether to precipitate, and washing.

2) Synthesis of Ang-PEG$_{3.4K}$-CPADN
Stirring Mal-PEG-CPADN (45 mg) and Angiopep-SH (50 mg) in DMSO at 37° C. overnight, dialyzing the resultant with water (3.5 K dialysis bag) for 48 h, followed by lyophilization, and detecting the amount of linked Angiopep by BCA.

3) Synthesis of polymer Ang-PEG$_{3.4K}$-PGPMA$_{4K}$ (in the same manner as in 2.1.3).

The 1H-NMR spectra of GPMA monomer, mPEG-CPADN, Mal-PEG-CPADN, mPEG-P (GPMA-FPMA) are as shown in FIG. 1.

3. Preparation of nanoparticles
3.1 Binding Cas9 with sgRNA: mixing Cas9 with sgRNA in a molar ratio of 1:1.2 at 10 mM HEPES (pH 7.4) buffer solution, standing at room temperature for 5 min.

3.2 Preparation of nanoparticles NP@Cas9/sgRNA: dissolving mPEG$_{2K}$-P (GPMA$_{4K}$, FPMA$_{0.6K}$) in 10 mM HEPES buffer solution, mixing the resultant with Cas9/sgRNA in a molar ratio of 1:2 and standing the mixture for 30 minutes to form NP@Cas9/sgRNA, wherein when sgRNA was sgPLK1, NP@Cas9/sgPLK1 was prepared.

3.3 Preparation of nanoparticles Ang-NP@Cas9/sgRNA: mixing and dissolving mPEG$_{2K}$-P (GPMA$_{4K}$, FPMA$_{0.6K}$) and Ang-PEG$_{3.4K}$-PGPMA$_{4K}$ in 10 mM HEPES buffer solution in a molar ratio of 1:4, then well mixing the resultant with Cas9/sgRNA at room temperature and standing for 30 minutes to form Ang-NP@Cas9/sgRNA, wherein when sgRNA was sgPLK1, Ang-NP@Cas9/sgPLK1 was prepared.

The nanodrugs used in Examples 2-4 are the nanodrug prepared in Example 1.

Example 2

Characterization Results of Nanodrug

Figure 2:
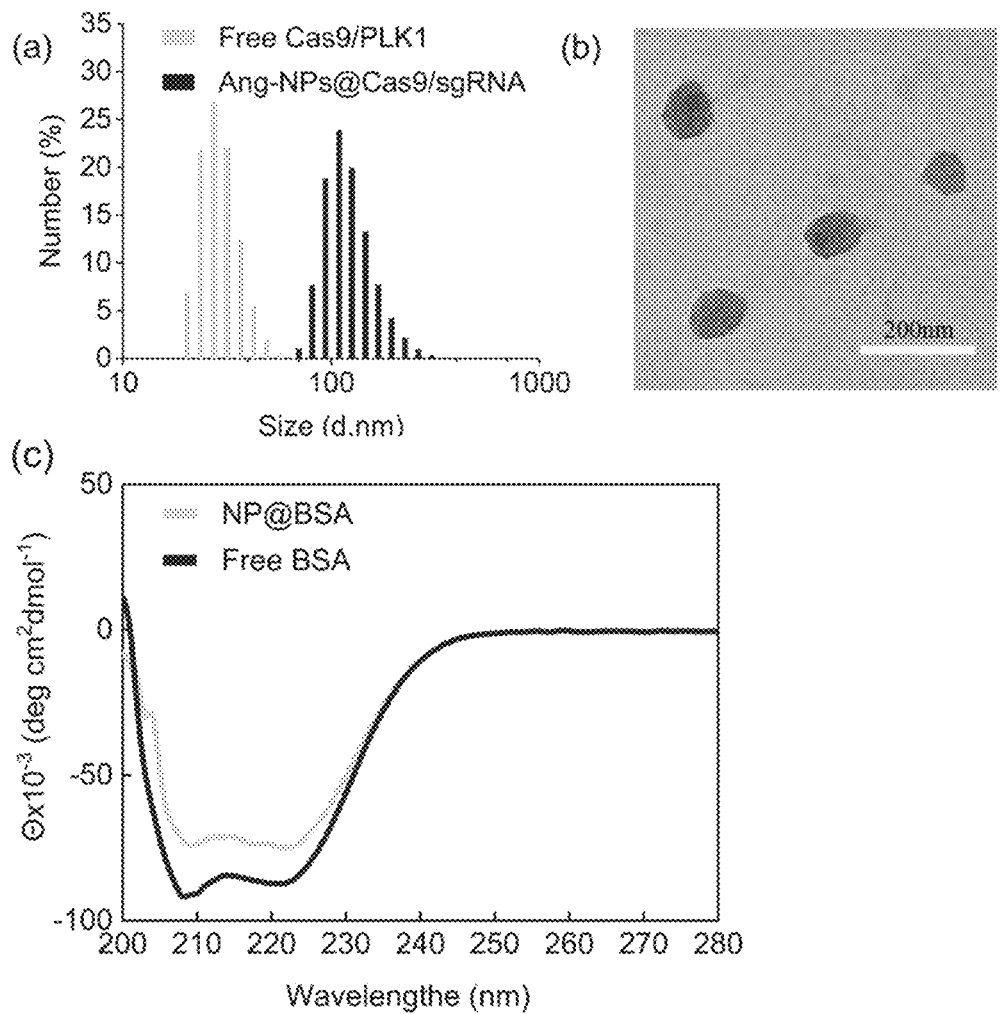
FIG. 2 shows a nanodrug characterization result, wherein (a) in FIG. 2 shows the particle size of the nanodrug, (b) in FIG. 2 shows a TEM image of the nanodrug, and (c) in FIG. 2 shows a circular dichroism detection result.

The particle size diagram of Ang-NP@Cas9/sgPLK1 and Free Cas9/sgPLK1 (i.e. Cas9/sgPLK1 complex) is as shown in (a) in FIG. 2, and the particle size and potential of the nanodrug are as shown in Table 1. In FIG. 2, (b) is a TEM image of Ang-NP@Cas9/sgPLK1. The particle size of the Cas9/sgPLK1 complex was about 30 nm, and negatively charged. After being wrapped by a polymer, the particle size was 149 nm, the stability was significantly enhanced, the uniformity was very good, and the surface had weak positive charges, which provided the possibility for the nanodrug to enter the body for the treatment of tumor.

TABLE 1

Particle Size and Potential of Nanodrug

|  | Free Cas9/sgPLK1 | Ang-NP@Cas9/sgPLK1 |
| --- | --- | --- |
| particle size (nm) | 28 | 149 |
| potential (mV) | −18.0 | 8.3 |
| PDI | 0.4 | 0.2 |

In FIG. 2, (c) shows a circular dichroism detection result. In the present example, the BSA protein was taken as an example, and the BSA protein was loaded by mPEG$_{2K}$-P (GPMA$_{4K}$, FPMA$_{0.6K}$) to prepare the nanodrug (NPs-BSA). Changes of peak values of Free BSA and NPs-BSA were compared under condition of 190-300 nm at 25° C. The results demonstrate that no protein surface structure was destroyed after mPEG$_{2K}$-P (GPMA$_{4K}$, FPMA$_{0.6K}$) bound protein, which indicates that the protein can play a role after binding to mPEG$_{2K}$-P (GPMA$_{4K}$, FPMA$_{0.6K}$).

In Examples 3 and 4, the effect of the nanodrug prepared in Example 1 was verified through cell level experiment and animal level experiment.

Example 3

Cell Level Experiment

1. Analysis of endocytosis through flow cytometry

In flow cytometry test, U87-Luc cells were inoculated in a 6-well cell culture plate (1×10$^5$ cells/well) to be cultured and adhered to the wall at 37° C. for 16-24 h, 300 μL of Free Cas9/sgPLK1, NP@Cas9/sgPLK1, Ang-NP@Cas9/sgPLK1, Ang-NP@Cas9/sgScr (Cas9 concentration was 10 nM) prepared by fluorescently labeled Cas9-Alexa647, and PBS was added, for culturing for 4 h, the samples were absorbed away, the cells were digested with 200 μL of pancreatin at 37° C. for 3 min, and 500 μL of fresh culture medium was added to stop the digestion. The resulting cell suspension was centrifuged at 1000×g for 3 minutes, washed twice with PBS, re-dispersed in 500 μL of PBS, and underwent a flow cytometer (BD FACS Calibur, Becton Dickinson, USA) test. In the above, sgScr refers to a negative control without a therapeutic effect.

Figure 3:
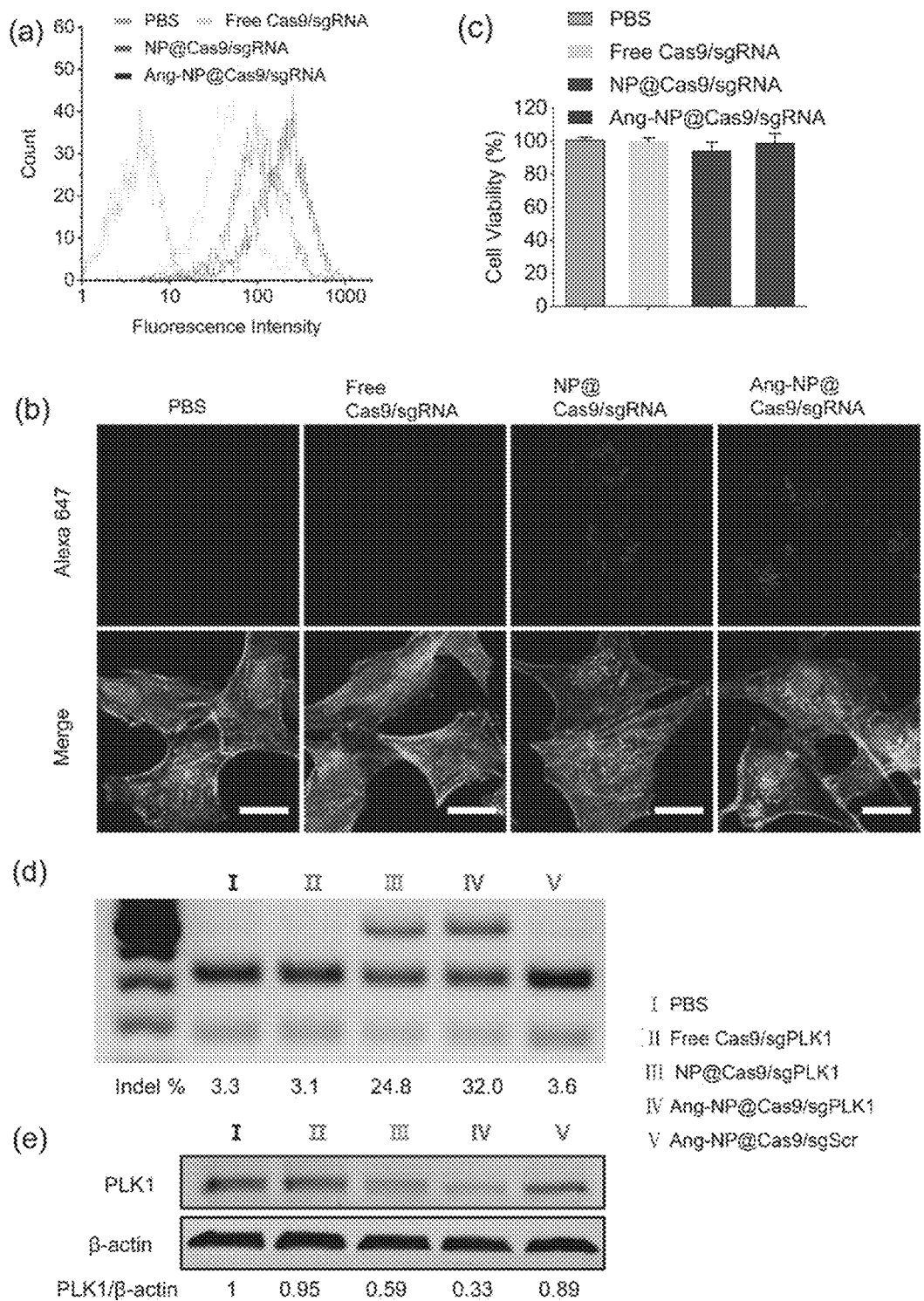
FIG. 3 shows experimental results of nanodrug in cell level, wherein (a) in FIG. 3 shows a flow cytometry detection result, (b) in FIG. 3 shows a confocal experiment result, (c) in FIG. 3 shows an MTT detection result, (d) in FIG. 3 shows a PLK1 gene knockout result, and (e) in FIG. 3 shows a protein expression result after the PLK1 gene is knocked out.

The detection result is as shown in (a) in FIG. 3, and it can be seen from (a) in FIG. 3 that Ang-NP@Cas9/sgPLK1 is proved to have a good targeting effect on U87-Luc cells.

2. Laser confocal microscope analysis 2.1 U87-Luc cells were plated into a 24-well cell culture plate containing microscope slides (5×10$^4$ cells/well) to be cultured for 24 h, then 300 UL of Free Cas9/sgPLK1, NP@Cas9/sgPLK1, Ang-NP@Cas9/sgPLK1 (Cas9 concentration was 50 nM), and PBS were added to incubate the cells for 4 h, and then the samples was prepared.

2.2 Fixation: the sample was washed with PBS three times and fixed with 4% paraformaldehyde at 37° C. for 15 min, then paraformaldehyde was sucked away, and the resultant was washed with PBS three times.

2.3 Cell staining 2.3.1 Phalloidine-FITC:

A. infiltration for 15 min with 0.1% TRITON X-100, washing for three times by PBS;

B. staining for 20-40 min with 10 μg/ml fluorescent phalloidin, washing for three times by PBS.

2.3.2 Hochest 33342 concentration was 10 μg/ml and staining lasted for 5-min.

The volume of liquid added was enough when the sample was submerged, for example, 200 μL of the liquid was added to a 24-well plate.

2.4 Sealing: a small amount (~5 μL) of an anti-fluorescence quencher was added on the glass slide, the side of the cover slip with cells was put close to the glass slide, and the glass slide was dried to be solidified, then placed in a confocal box and stored in a light-tight condition.

The result of confocal experiment is as shown in (b) in FIG. 3, and it can be seen from (b) in FIG. 3 that Ang-NP@Cas9/sgPLK1 can enter cells well, and can successfully enter nucleus to provide possibility for gene editing.

3. Detecting cytotoxicity of nanodrug by MTT method

MTT detection result is as shown in (c) in FIG. 3, and it can be seen from (c) in FIG. 3 that Ang-NP@Cas9/sgPLK1 has quite little toxicity to cells, and has very good biocompatibility.

4. Detecting the nanodrug gene editing effect by restriction endonuclease method 4.1 Transfection 1) Plating U87-Luc cells in a 24-well plate (5×10$^4$ cells/well) with cells being adhered to the wall for 16-24 h.

2) Adding 300 μL of Free Cas9/sgPLK1, NP@Cas9/sgPLK1, Ang-NP@Cas9/sgPLK1, Ang-NP@Cas9/sgScr (Cas9 concentration was 50 nM) to incubate the cells for 6 h, then replacing the culture medium with a fresh culture medium, and continuing the culturing for 72 h, and then collecting the cells. In the above, sgScr refers to a negative control without a therapeutic effect.

4.2 Extraction of genomes

The cell genomes were extracted using a kit after collection of cells.

4.3 Amplification of PLK1 genomic fragments by PCR technology

The target fragments were subjected to PCR using a high-fidelity enzyme, wherein a PCR reaction system is as shown in the table below.

|  |  |
| --- | --- |
| ddH$_2$O | Making up to 100 µL |
| 10 × KOD Buffer | 10 µL |
| 2.5 mM dNTP | 10 µL |
| MgSO$_4$ | 6 µL |
| primer PLK1 sur F | 3 µL |
| primer PLK1 sur R | 3 µL |
| template | 500 ng |
| KODneo-plus enzyme | 2 µL |

4.4 Verification of editing effect at gene level through enzyme digestion

The PCR fragment was subjected to enzyme digestion using BstAP I (R0654S) of NEB, followed by 2% agarose electrophoresis, then images were collected by a gel imager, and finally the editing efficiency was analyzed grayscale using image J software.

PLK1 gene knockout result is as shown in (d) in FIG. 3, and it can be seen from (d) in FIG. 3 that the effect of 32% may reach at the gene level.

5. Exploring the effect of Cas9 gene editing on protein expression by Western Blot 5.1 Transfection 1) Plating the U87-Luc cells in a 6-well plate (1×10$^5$ cells/well) and enabling the cells to be adhered to the wall for 16-24 h.

2) Adding 500 µL of Free Cas9/sgPLK1, NP@Cas9/sgPLK1, Ang-NP@Cas9/sgPLK1, and Ang-NP@Cas9/sgScr (Cas9 concentration was 50 nM) to incubate with the cells for 6 h, then replacing the culture medium with a fresh culture medium, and continuing the culturing for 96 h, and then collecting the cells. In the above, sgScr refers to a negative control without a therapeutic effect.

5.2 Extraction of cell holoprotein

1) Lysing protein using RIPA containing PMSF (strong), and collecting protein samples.

5.3 Run the gel

1) Protein denaturation: denaturing the protein samples at 100° C. for 5 min.

2) Electrophoresis using 10% SDS-PAGE gel.

3) Transferring (300 mA, 30 min).

4) Blocking (5% defatted milk, room temperature, 2 h).

5) Incubating primary antibodies (4° C., overnight).

6) Incubating secondary antibodies (incubating with fluorescently labeled secondary antibodies at room temperature for 1 h).

5.4 Development

Results are as shown in (e) in FIG. 3, and the Western Blot verifies that the amount of protein expression was reduced after PLK1 gene was knocked out, and finally the amount of protein expression can be reduced to 33% after the nanodrug gene editing.

Example 4

Animal Level Experiment

1. Pharmacokinetics experiment

Pharmacokinetic analyses of Free Cas9/sgPLK1, NP@Cas9/sgPLK1, and Ang-NP@Cas9/sgPLK1 in the body of mice were compared, BALB/c mice of 6-8 weeks were randomly grouped (3 mice in each group), and after tail intravenous injection of the drug, blood was taken from eyes with a capillary pipette at 3 min, 5 min, 10 min, 15 min, 20 min, 30 min, 45 min, 60 min, 1.5 h, 2 h, 3 h, 4 h, 6 h, 8 h, and 10 h.

Figure 4:
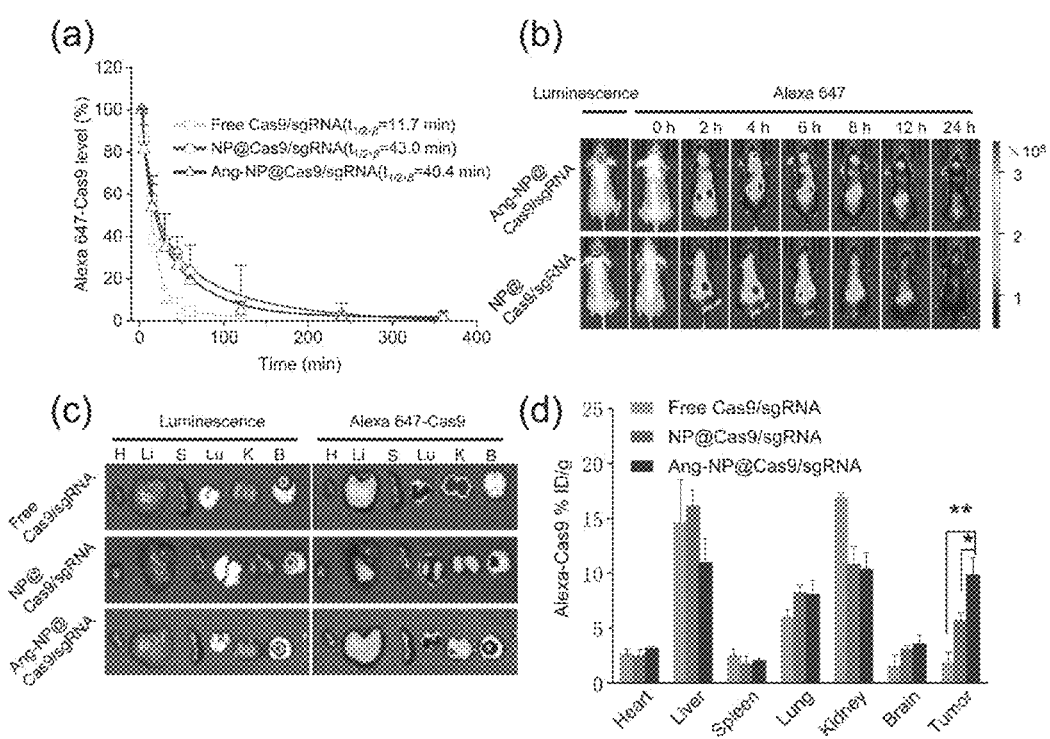
FIG. 4 shows experimental results of nanodrug in animal level, wherein (a) in FIG. 4 shows a result of in-vivo pharmacokinetic studies, (b) in FIG. 4 shows the tumor targeting effect of nanodrug, and (c) and (d) in FIG. 4 show the distribution of the nanodrug in each organ in the mice.

Results of in vivo pharmacokinetic studies are as shown in (a) in FIG. 4, and it can be seen from (a) in FIG. 4 that the circulation time of Ang-NP@Cas9/sgPLK1 in the body is relatively long, equivalent to that of NP@Cas9/sgPLK1 ((a) in FIG. 4), and longer than that of Free Cas9/sgPLK1, indicating that Ang-NP@Cas9/sgPLK1 has a longer blood circulation time, which prolongs the circulation time of the drug in the blood.

2. Penetrating BBB and tumor targeting effect of nanodrug in the body of mice

Establishment of in situ model of U87-Luc cerebral glioma was realized through transplantation of tumor tissues in the brain of BALB/c nude mice (18-20 g, aged 6-8 weeks). Two groups Ang-NP@Cas9/sgPLK1 and NP@Cas9/sgPLK1 were selected to compare, each mouse was injected with Cas9 in an amount of 15 µg, with 3 mice in each group, a small animal imager was used for fluorescence irradiation at 0 h, 2 h, 4 h, 6 h, 8 h, 12 h, and 24 h, respectively, and the fluorescence intensity of the nanoparticles was observed to judge the tumor targeting effect of the nanodrug, and the result is as shown in (b) in FIG. 4.

From the fluorescence intensity, it can be seen that Ang-NP@Cas9/sgPLK1 has relatively strong fluorescence intensity at the brain of the animals, indicating that Ang-NP@Cas9/sgPLK1 has a very good effect of penetrating BBB and targeting tumors in vivo.

3. Distribution of nanodrug in each organ in mice

Establishment of the in situ model of U87-Luc cerebral glioma was realized through transplantation of tumor tissues in the brain of BALB/c nude mice (18-20 g, aged 6-8 weeks). Three groups Free Cas9/sgPLK1 (Cas9-Alexa), NP@Cas9/sgPLK1, and Ang-NP@Cas9/sgPLK1 were selected to compare, each mouse was injected with Cas9 in an amount of 0.8 mg/kg, with three mice in each group. The mice were administered by tail intravenous injection. At 4 h, the mice were sacrificed, and heart, liver, spleen, lung, kidney, brain and tumor were taken and subjected to fluorescence irradiation using a small animal imager (results are as shown in (c) in FIG. 4), and the tissues were crushed, and the nanoparticle concentration in the tissues was measured (the result is as shown in (d) in FIG. 4).

According to the fluorescence intensity, the distribution of nanoparticles in the heart, liver, spleen, lung, kidney, brain and tumor can be observed. Ang-NP@Cas9/sgPLK1 has relatively strong fluorescence at the tumor sites, indicating that Ang-NP@Cas9/sgPLK1 has a very good tumor targeting effect. The tissues were crushed, to measure the nanoparticle concentration in the tissues, and the concentration of specific distribution of Ang-NP@Cas9/sgPLK1 in the heart, liver, spleen, lung, kidney, brain and tumor can be accurately analyzed. The accumulation of Ang-NP@Cas9/sgPLK1 at the tumor sites might reach 9.8 ID %/g, having better cumulative amount than other control groups.

Finally, it should be explained that the various examples above are merely used for illustrating the technical solutions of the present disclosure, rather than limiting the present disclosure; while the detailed description is made to the present disclosure with reference to various preceding example, those ordinarily skilled in the art should understand that they still could modify the technical solutions recited in various preceding embodiments, or make equivalent substitutions to some or all of the technical features therein; these modifications or substitutions do not make the corresponding technical solutions essentially depart from the scope of the technical solutions of the various examples of the present disclosure.

Besides, a person skilled in the art could understand that although some examples herein include certain features included in other examples rather than other features, combinations of features in different examples means that they fall within the scope of the present disclosure and form different examples. For example, in the following claims, any of the examples claimed to protect can be used in any combination manner. Information disclosed in the part of Background Art merely aims at deepening understanding to the overall background art of the present disclosure, but should not be regarded as acknowledging or implying in any form that the information constitutes prior art generally known by a person skilled in the art.

What is claimed is:

1. A drug carrier, comprising a polymer mPEG-P (GPMA, FPMA) and a polymer Ang-PEG-PGPMA, wherein a structural formula of the mPEG-P (GPMA, FPMA) is:

a structural formula of the polymer Ang-PEG-PGPMA is:

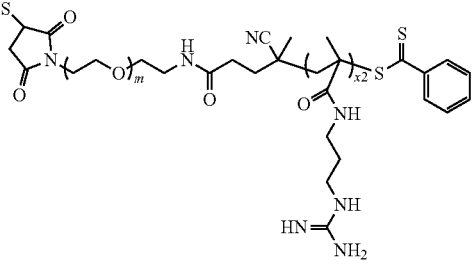

where n is 35-45, x1 is 15-20, y is 2-4, m is 75-85, and x2-x1.

2. The drug carrier according to claim 1, wherein the polymer mPEG-P (GPMA, FPMA) is $mPEG_{2K}$-P ($GPMA_{3K-4K}$, $FPMA_{0.5K-1K}$).

3. The drug carrier according to claim 1, wherein the polymer Ang-PEG-PGPMA is $Ang-PEG_{3.4K}$-$PGPMA_{4K}$.

* * * * *

UNITED STATES PATENT AND TRADEMARK OFFICE
CERTIFICATE OF CORRECTION

PATENT NO. : 12,161,700 B2
APPLICATION NO. : 17/112020
DATED : December 10, 2024
INVENTOR(S) : Weimin Ruan et al.

Page 1 of 1

It is certified that error appears in the above-identified patent and that said Letters Patent is hereby corrected as shown below:

In the Claims

Column 20, Line 32, Claim 1 "x2-x1" should read "x2=x1"

Signed and Sealed this
Fourth Day of February, 2025

Coke Morgan Stewart
*Acting Director of the United States Patent and Trademark Office*